(12) United States Patent
Oliveira et al.

(10) Patent No.: US 10,781,363 B2
(45) Date of Patent: Sep. 22, 2020

(54) EMULSIFIED ACIDIC TREATMENT FLUID WITH SURFACE MODIFICATION AGENTS

(71) Applicant: Halliburton Energy Services, Inc., Houston, TX (US)

(72) Inventors: Humberto Almeida Oliveira, Bairro Joa (BR); Zheng Lu, Kingwood, TX (US); Yuming Yang, Houston, TX (US); Venkata Satya Srikalyan Bhamidipati, Kingwood, TX (US); Kristina Henkel Holan, Cypress, TX (US)

(73) Assignee: Hallibunon Energy Services, Inc., Houston, TX (US)

(*) Notice: Subject to any disclaimer, the term of this patent is extended or adjusted under 35 U.S.C. 154(b) by 0 days.

(21) Appl. No.: 15/525,539

(22) PCT Filed: Dec. 31, 2014

(86) PCT No.: PCT/US2014/073015
§ 371 (c)(1),
(2) Date: May 9, 2017

(87) PCT Pub. No.: WO2016/108895
PCT Pub. Date: Jul. 7, 2016

(65) Prior Publication Data
US 2017/0335175 A1    Nov. 23, 2017

(51) Int. Cl.
| | | |
|---|---|---|
| C09K 8/82 | (2006.01) | |
| C09K 8/74 | (2006.01) | |
| E21B 43/26 | (2006.01) | |
| C07C 11/00 | (2006.01) | |
| C07C 211/62 | (2006.01) | |

(52) U.S. Cl.
CPC .............. C09K 8/74 (2013.01); E21B 43/26 (2013.01); C07C 11/00 (2013.01); C07C 211/62 (2013.01); C09K 8/82 (2013.01)

(58) Field of Classification Search
CPC ... C09K 8/36; C09K 8/68; C09K 8/74; C09K 8/52; C09K 8/90; C09K 8/88; C09K 8/035; C09K 8/70; C09K 8/72; C09K 8/26; C09K 8/32; C09K 8/12; C09K 8/528; C09K 8/54; C09K 8/08; C09K 8/508; C09K 8/514; C09K 8/524; C09K 8/92; C09K 8/28; C09K 8/62; C09K 8/76; C09K 8/64; C09K 8/80; C09K 8/03; C09K 8/50; C09K 8/518; C09K 8/66; C09K 8/703; C09K 8/78; C09K 8/82; C09K 8/94; C09K 8/502; C09K 8/512; C09K 8/565; C09K 8/572; C09K 8/58; C09K 8/588; C09K 8/805; C09K 8/86; E21B 43/26; E21B 43/25; E21B 43/267; E21B 21/003; E21B 37/08; E21B 41/0064; E21B 43/16; E21B 43/164; E21B 47/00; E21B 47/1015; E21B 21/00; E21B 31/00; E21B 37/00; E21B 37/06; E21B 43/283

See application file for complete search history.

(56) References Cited

U.S. PATENT DOCUMENTS

| 4,233,165 A * | 11/1980 | Salathiel | C09K 8/50 166/271 |
|---|---|---|---|
| 8,101,556 B2 | 1/2012 | Norman et al. | |
| 8,669,212 B2 | 3/2014 | Norman et al. | |
| 9,222,013 B1 * | 12/2015 | Champagne | C09K 8/584 |
| 2007/0215347 A1 * | 9/2007 | Tang | C09K 8/584 166/263 |
| 2008/0230095 A1 * | 9/2008 | McKechnie | C11D 1/521 134/42 |
| 2012/0181019 A1 * | 7/2012 | Saini | B82Y 30/00 166/250.01 |
| 2014/0116695 A1 | 5/2014 | Maghrabi et al. | |
| 2015/0114646 A1 * | 4/2015 | Price Hoelscher | E21B 33/138 166/302 |

FOREIGN PATENT DOCUMENTS

| WO | 2010/128270 | 11/2010 |
|---|---|---|
| WO | 2013116198 | 8/2013 |
| WO | WO2013/116198 | * 8/2013 |

OTHER PUBLICATIONS

SPE 147306, Wettability Alteration in High Temperature and High Salinity Carbonate Reservoirs by Sharma et al. fdated Oct. 30, 2011.
SPE 113407, Wettability Alteration of Fractured Carbonate Reservoirs by Gupta et al. dated Apr. 19, 2008.
Surfactant Induced Reservoir Wettability Alteration: Recent theoretical and experimental advances in enhanced oil recovery by Yefei et al. dated Dec. 8, 2011.
SPE 124822, Surfactant Screening for Wettability Alteration in Oil-Wet Fractured Carbonates by Gupta et al. dated Oct. 4, 2009.
SPE-169125-MS, Wettability Alteration in High Temperature Carbonate Reservoirs by Chen et al. dated Apr. 12, 2014.
SPE 165348, Weakly Emulsifying Surfactant Reduces Formation Damage and Enhances Well Productivity in Acid Stimulation by Liang Xu, dated Apr. 19, 2013.
SPE 141205, Effect of Surfactants on Water Imbibition into Heterogeneous Carbonate Rocks at an Elevated Temperature dated Sep. 25, 2011.
SPE 166129, Visualization and Analysis of Surfactant Imbibition into Oil-Wet Fractured Cores by Mirzaei et al. dated Sep. 30, 2013.
Oilfield Review, Fundamentals of Wettability dated Jun. 1, 2007.
International Search Report and Written Opinion for Application No. PCT/US2014/073015 dated Aug. 31, 2015.

* cited by examiner

*Primary Examiner* — Kumar R Bhushan
(74) *Attorney, Agent, or Firm* — Thomas Rooney; C. Tumey Law Group PLLC

(57) ABSTRACT

Surface modification agents may be included in emulsified acidic treatment fluids to leave surfaces in carbonate formations water wet after acidizing operations. A method of acidizing a subterranean formation, comprising: providing a treatment fluid in the form of an invert emulsion, wherein the treatment fluid comprises: a hydrocarbon phase comprising an oil-soluble liquid and an emulsifier; and an aqueous acidic phase comprising water, an acid, and a surface modification agent; and introducing the treatment fluid into a wellbore.

11 Claims, 1 Drawing Sheet

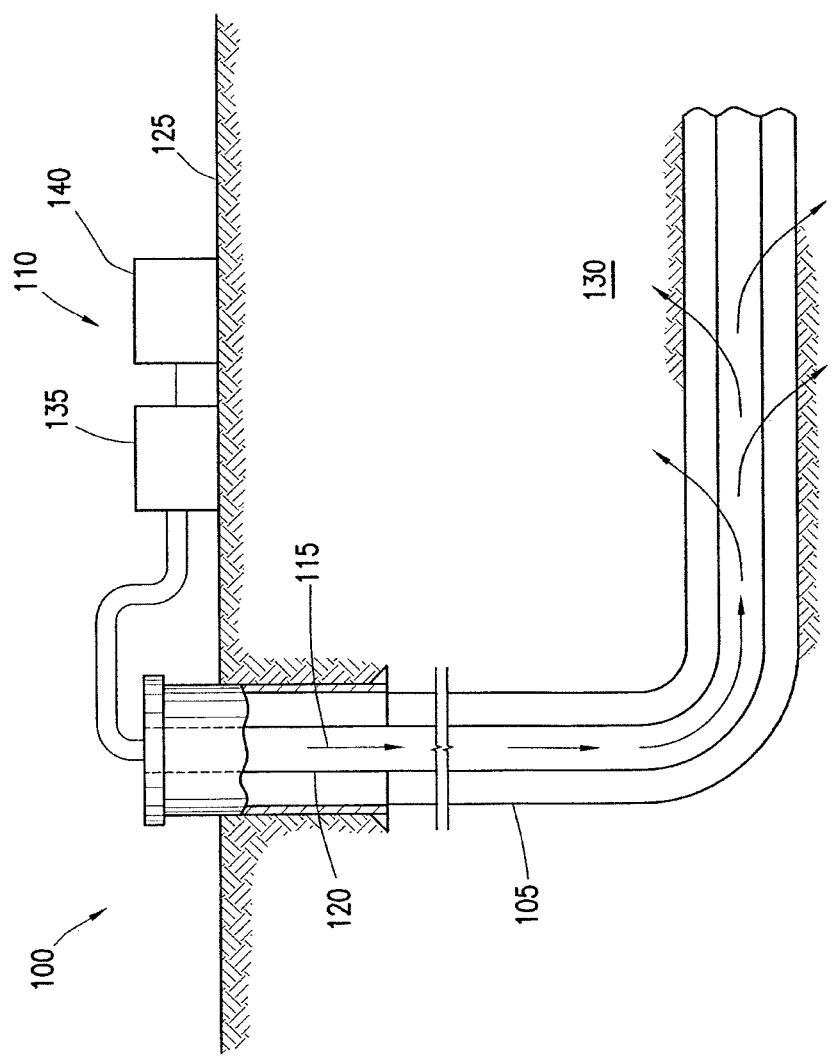

US 10,781,363 B2

EMULSIFIED ACIDIC TREATMENT FLUID WITH SURFACE MODIFICATION AGENTS

BACKGROUND

Embodiments are directed to emulsified acidic treatment fluids and, more particularly, embodiments are directed to inclusion of surface modification agents in emulsified acidic treatment fluids to leave surfaces in carbonate formations water wet after acidizing operations.

The production of desirable fluids (e.g., oil and gas) from subterranean formations may often be enhanced by stimulating a region of the formation surrounding a well bore. Where the subterranean formation comprises acid-soluble components, such as those present in carbonate and sandstone formations that contain a percentage of soluble material, stimulation is often achieved by contacting the formation with a treatment fluid comprising an acid. This can accomplish a number of purposes, which can be, for example, to help remove residual fluid material or filtercake damage or to increase the permeability of the subterranean formation. One method of acidizing, known as "fracture acidizing," comprises injecting an acidic treatment fluid into the formation at a pressure sufficient to create or enhance one or more fractures within the subterranean formation. Another method of acidizing, known as "matrix acidizing," comprises injecting the acidic treatment into the formation at a pressure below that which would create or enhance one or more fractures within the subterranean formation. The use of the term "acidizing" herein refers to both matrix and fracture types and, more specifically, refers to the general process of introducing an acid downhole to perform a desired function.

One of conventional types of acidic treatment fluid is an emulsified acid in the form of a water-in-oil emulsion that contains a continuous hydrocarbon phase and an internal aqueous acidic phase. By emulsifying of the acid in oil, the acid should be slower reacting thus increasing the length of penetration (wormhole length) into the formation. These emulsified acidic treatment fluids have been used in the stimulation of carbonate formations. However, because carbonate formations tend to be naturally oil wet, their production may not reach desirable levels unless treatments are applied to change the surfaces to water wet.

BRIEF DESCRIPTION OF THE DRAWINGS

These drawings illustrate certain aspects of some of the examples of the present method and should not be used to limit or define the method.

The FIGURE is a schematic illustration of an example system for delivery of treatment fluids into a wellbore.

DETAILED DESCRIPTION

Embodiments are directed to emulsified acidic treatment fluids and, more particularly, embodiments are directed to inclusion of surface modification agents in emulsified acidic treatment fluids to leave surfaces in carbonate formations water wet after acidizing operations.

There may be several potential advantages to the methods and compositions disclosed herein, only some of which may be alluded to herein. One of the many potential advantages is that, because surface modification agents may be included in the emulsified acidic treatments fluids, the carbonate formation may be left water wet after acidizing instead of naturally oil wet as usually occurs in most carbonate formations. Yet another potential advantage is that the surface modification agents may also minimize capillary pressure in the formation. Thus, surface modification agents may be included in emulsified acidic treatment fluids to change wettability of carbonate formations from naturally oil wet to water wet and minimize capillary pressure, thus potentially increasing the percentage spent acid flow back and hydrocarbons/reservoir recovery.

The treatment fluids may generally be in the form of an invert emulsion that comprises a hydrocarbon phase (e.g., oil phase) and an aqueous acidic phase in which the hydrocarbon phase is the continuous phase and the aqueous acidic phase is the internal phase. The hydrocarbon phase may comprise an oil-soluble liquid (e.g., synthetic oils, kerosene, solvents mixture, diesel etc.) and an emulsifier. The aqueous acidic phase may comprise water, an acid, and a surface modification agent, Additional additives that are commonly used in acidizing operations may also be included in the treatments fluids as should be apparent to those of ordinary skill, with the benefit of this disclosure. For example, optional additives (e.g., iron control agents, corrosion inhibitors, etc.) may be included in the aqueous acidic phase as should be appreciated by those of ordinary skill in the art.

The hydrocarbon phase can include an oil-soluble liquid, such as one or more suitable oils or organic solvents. The hydrocarbon phase may include hydrocarbon liquids as wells as hydrocarbons in which one or more hydrogen atoms have been removed, such as xylene. The oil may include a natural or synthetic oil-soluble liquid, which may include a natural or synthetic source of oil. Examples oil-soluble liquids may include, without limitation, kerosene, diesel oils, crude oils, gas oils, fuel oils, paraffin oils, mineral oils, olefinic hydrocarbons, aromatic hydrocarbons, glyceride triester, other petroleum distillates, and any combination thereof. Examples of synthetic oil-soluble liquids may include, without limitation, polyolefins, polydiorganosiloxanes, siloxanes, and organosiloxanes. The hydrocarbon phase may have a viscosity of less than 200 cP and optionally less than 20 cP. The ratio of the hydrocarbon phase to the water phase, in a water-in-oil emulsion, for example, may be in the range of 20:80 v/v OWR (oil to water ratio) to 90:10 or, alternatively 20:80 v/v OWR to 50:50 v/v OWR. The hydrocarbon phase can be any suitable vol % of the invert emulsion. For example, the hydrocarbon phase can be about 1 vol % to about 99 vol % of the invert emulsion, about 10 vol % to about 50 vol %, or about 1 vol % or less, or about 2 vol %, 3, 4, 5, 6, 8, 10, 12, 14, 16, 18, 20, 25, 30, 35, 40, 45, 50, 55, 60, 65, 70, 75, 80, 85, 90, 91, 92, 93, 94, 95, 96, 97, 98, or about 99 vol % or more of the invert emulsion.

The hydrocarbon phase may further comprise a suitable organic solvent, such as an aromatic hydrocarbon composition. The aromatic hydrocarbon composition may be suitable for asphaltene dissolution. The aromatic hydrocarbon composition may be used along or in combination with one or more of the other oil-soluble liquids disclosed herein. The aromatic hydrocarbon composition may include at least one of benzene, toluene, ethyl benzene, or xylenes. The aromatic hydrocarbon composition may include aromatic petroleum naptha. The aromatic hydrocarbon composition or the aromatic petroleum naptha may include a mono or poly($C_0$-$C_{10}$)alkyl-substituted ($C_5$-$C_{30}$)aromatic hydrocarbon ring system, wherein each alkyl is independently substituted or unsubstituted, and wherein each aromatic ring is independently substituted or unsubstituted. The aromatic hydrocarbon composition or the aromatic petroleum naptha may include at least one of mono($C_1$-$C_{10}$)alkyl-substituted benzene, poly($C_1$-$C_{10}$)alkyl-substituted benzene, mono($C_1$-$C_{10}$)

alkyl-substituted naphthalene, and poly($C_1$-$C_{10}$)alkyl-substituted naphthalene. The aromatic hydrocarbon composition or the aromatic petroleum naptha may include heavy aromatic petroleum naphtha, e.g., having a boiling point range of about 165° C. to about 290° C. The aromatic hydrocarbon composition may include any suitable proportion of the aromatic petroleum naptha, such as about 5 wt % to about 100 wt % aromatic petroleum naptha, or about 60 wt % to about to about 100 wt %, or about 5 wt % or less, or about 10 wt %, 15, 20, 25, 30, 35, 40, 45, 50, 55, 60, 65, 70, 75, 80, 85, 90, 95, 96, 97, 98, 99, or about 100 wt % aromatic petroleum naptha. In some embodiments, about 60 wt % to about 100 wt % of the aromatic hydrocarbon composition may be heavy aromatic petroleum naphtha.

The aromatic hydrocarbon composition may include a $C_{10}$-$C_{22}$ compound that has fused aromatic hydrocarbon rings. The $C_{10}$-$C_{22}$ compound may be at least one of naphthalene, anthracene, phenanthrene, chrysene, or pyrene. The aromatic hydrocarbon composition may comprise the $C_{10}$-$C_{22}$ compound in an amount of about 0.1 wt % to about 40 wt %, or about 2 wt % to about 20 wt %, or about 0.1 wt % or less, or about 1 wt %, 2, 3, 4, 5, 6, 7, 8, 9, 10, 12, 15, 18, 20, 25, 30, 35, or about 40 wt %. In some embodiments, about 5 wt % to about 10 wt % of the aromatic hydrocarbon composition is naphthalene.

The aromatic hydrocarbon composition may include at least one of a di($C_1$-$C_5$)alkylbenzene and a tri($C_1$-$C_5$)alkylbenzene, such as at least one of trimethylbenzene, triethylbenzene, dimethylbenzene, diethylbenzene, methylethylbenzene, dimethylethylbenzene, and diethylmethylbenzene, having substitution patterns of at least one of 1,2-, 1,3-, 1,4-, 1,2,3-, 1,2,4-, 1,2,5-, 1,3,5-, and 1,3,6-. The aromatic hydrocarbon composition may comprise at least one of a di($C_1$-$C_5$)alkylbenzene and a tri($C_1$-$C_5$)alkylbenzene in an amount of about 0.1 wt % to about 20 wt %, or about 0.5 wt % to about 10 wt %, or about 0.5 wt % or less, or about 1 wt %, 2, 3, 4, 5, 6, 7, 8, 9, 10, 12, 14, 16, 18, or about 20 wt % or more. The aromatic hydrocarbon composition may comprise 1,2,4-trimethylbenzene in an amount of about 1 wt % to about 5 wt %.

The aromatic hydrocarbon composition may comprise about 60 wt % to about 100 wt % heavy aromatic petroleum naphtha, about 5 wt % to about 10 wt % naphthalene, and about 1 wt % to about 5 wt % 1,2,4-trimethylbenzene.

The aromatic hydrocarbon composition may include xylenes, or include at least one of 1,2-dimethylbenzene, 1,3-dimethylbenzene, and 1,4-dimethylbenzene, such as about 10 wt % to about 100 wt % of the aromatic hydrocarbon composition, or about 30 wt % to about 100 wt %, or about 10 wt % or less, or about 20 wt %, 30, 40, 50, 60, 70, 80, 90, or about 100 wt % of the aromatic hydrocarbon composition. For example, about 60-100 wt % of the aromatic hydrocarbon composition may comprise xylenes. By way of further example, about 60-100 wt % of the aromatic hydrocarbon composition may include xylenes, and about 10 wt % to about 30 wt % of the aromatic hydrocarbon composition may include ethylbenzene.

The aromatic hydrocarbon composition may include a ($C_1$-$C_5$)alkylbenzene, such as ethylbenzene. For example, about 1 wt % to about 80 wt % of the aromatic hydrocarbon composition can be the ($C_1$-$C_5$)alkylbenzene, or about 5 wt % to about 60 wt %, or about 1 wt % or less, or about 5, 10, 15, 20, 25, 30, 35, 40, 45, 50, 55, 60, 65, 70, 75, or about 80 wt % or more of the composition can be the ($C_1$-$C_5$)alkylbenzene. By way of further example, about 10 wt % to about 30 wt % of the aromatic hydrocarbon composition is ethylbenzene.

The hydrocarbon phase may further include one or more polar organic solvents that may be oil-soluble. The polar organic solvent may be used alone or in combination with one or more of the oil-soluble liquids described herein. The polar organic solvent may be any suitable polar organic solvent such that the emulsion can be used as described herein. The polar organic solvent may be a solvent designed for asphaltene dissolution and can give the hydrocarbon phase of the emulsion asphaltene-dissolving properties. For example, the polar organic solvent may include at least one of acetone, chloroform, cichloromethane, tetrahydrofuran, ethyl acetate, acetone, dimethylformamide, acetonitrile, dimethyl sulfoxide, propylene carbonate, formic acid, n-butanol, isopropanol, n-propanol, ethanol, methanol, acetic acid, nitromethane, or N-methylpyrrolidone. Any suitable proportion of the treatment fluid may be the polar organic solvent. For example, about 0.01 wt % to about 90 wt % of the treatment fluid may be the one or more polar organic solvents, or about 0.1 wt % to about 5 wt %, or about 0.01 wt % or less, or about 0.05 wt %, 0.1, 0.5, 1, 1.2, 1.4, 1.6, 1.8, 2.0, 2.2, 2.4, 2.6, 2.8, 3, 3.5, 4, 5, 6, 7, 8, 9, 10, 15, 20, 25, 30, 35, 40, 45, 50, 55, 60, 65, 70, 75, 80, 85, or about 90 wt % or more of the invert emulsion may be the one or more polar organic solvents.

An emulsifier may be present in the hydrocarbon phase of the treatment fluid. The emulsifier may be soluble in the hydrocarbon phase of the invert emulsion. In general, the emulsifier is typically a surfactant or mixture of surfactants that functions to stabilize the invert emulsion, for example, by preventing the droplets of the dispersed phase from flocculating or coalescing in the emulsion. It is believed that surfactants may stabilize the emulsion by concentrating at and being adsorbed onto the interface of the hydrocarbon phase and the aqueous acidic phase.

The emulsifier can be any suitable proportion of the emulsion, such that the invert emulsion can be formed and can be used as described herein. For example, the emulsifier can be about 0.001 wt % to about 25 wt % of the emulsion, or about 0.01 wt % to about 10 wt %, or about 0.1 wt % to about 5 wt %, or about 0.001 wt % or less, or about 0.01 wt %, 0.05, 0.1, 0.2, 0.4, 0.6, 0.8, 1, 1.2, 1.4, 1.6, 1.8, 2, 2.2, 2.4, 2.6, 2.8, 3, 3.2, 3.4, 3.6, 3.8, 4, 4.5, 5, 6, 7, 8, 9, 10, 15, 20, or about 25 wt % or more of the invert emulsion.

The emulsifier may be any suitable emulsifier, such that the invert emulsion can be formed and can be used as described herein. Examples of suitably emulsifiers may include at least one of a sulfate, sulfonate, phosphate, carboxylate, tri($C_1$-$C_{10}$)alkylammonium halide, substituted or unsubstituted fatty alcohol, substituted or unsubstituted fatty acid, substituted or unsubstituted fatty acid ester, and a substituted or unsubstituted poly(($C_1$-$C_{10}$)hydrocarbylene oxide) independently having H or ($C_1$-$C_{10}$)hydrocarbylene as end-groups. Additional examples of suitable emulsifiers may include ammonium aluryl sulfate, sodium lauryl sulfate, sodium laureth sulfate, sodium myreth sulfate, dioctyl sodium sulfosuccinate, perfluorooctanesulfonate, perfluorobutanesulfonate, linear ($C_1$-$C_{10}$)alkylbenzene sulfonate, sodium stearate, sodium lauroyl sarcosinate, perfluorononanoate, perfluorooctanoate, octenidine dihydrochloride, cetyl trimethyl ammonium bromide, cetyl trimethylammonium chloride, cetylpyridinium chloride, benzalkonium chloride, benzethonium chloride, 5-bromo-5-nitro-1,3-dioxane, dimethyldiactadecylammonium chloride, cetrimonium bromide, dioctadecyldimethylammonium bromide, 3-[(3-cholamidopropyl)dimethylammonio]-1-propanesulfonate, cocamidopropyl hydroxysultaine, cocamidopropyl betaine, lecithin, a polyoxyethylene glycol alkyl ether (e.g. octaethylene glycol monododecyl ether, pentaethylene glycol monododecyl ether), a polyoxypropylene glycol ether, a glucoside alkyl ether (e.g., decyl glucoside, lauryl glucoside, octyl glucoside), a polyoxyethylene glycol octylphenol ether (e.g., triton X-100), a polyoxyethylene glycol alkylphenol ether (e.g., nonoxynol-9), a glycerol alkyl ether (e.g., glyceryl laurate), a polyoxyethylene glycol sorbitan alkyl ester (e.g., polysorbate, such as polyoxyethylene (20) sorbitan monolaurate, or monopalmitate, or monosterate, or monooleate), cocamide monoethanolamine, cocamide diethanolamine, dodecyldimethylaminde oxide, a poloxamer, and a polyethoxylated tallow amine.

The emulsifier may include at least one of a polyaminated fatty acid or a polyaminated fatty acid alkyl ester, for example, at least one of a polyaminated ($C_3$-$C_{50}$)fatty acid or a polyaminated ($C_3$-$C_{50}$)fatty acid ($C_1$-$C_{10}$)alkyl ester. For example, about 1 wt % to about 100 wt % of the emulsifier can be at least one of a polyaminated fatty acid or a polyaminated fatty acid alkyl ester, or about 50 to about 90 wt %, or about 1 wt % or less, or about 5, 10, 15, 20, 25, 30, 35, 40, 45, 50, 55, 60, 65, 70, 75, 80, 85, or about 90 wt % or more.

The emulsifier may include ethylene glycol monobutyl ether, such as about 0.01 wt % to about 20 wt % ethylene glycol monobutyl ether, or about 1 wt % to about 5 wt %, or about 0.01 wt % or less, or about 0.1 wt %, 1, 2, 3, 4, 5, 6, 7, 8, 9, 10, 12, 14, 16, 18, or about 20 wt % or more.

The emulsifier may include diethylene glycol monobutyl ether, such as about 0.01 wt % to about 20 wt % diethylene glycol monobutyl ether, or about 1 wt % to about 5 wt %, or about 0.01 wt % or less, or about 0.1 wt %, 1, 2, 3, 4, 5, 6, 7, 8, 9, 10, 12, 14, 16, 18, or about 20 wt % or more.

The emulsifier may include a petroleum distillate, such as a hydrotreated light petroleum distillate. By way of example, the emulsifier may include about 1 wt % to about 90 wt % hydrotreated light petroleum distillate, or about 10 wt % to about 30 wt % hydrotreated light petroleum distillate, or about 1 wt % or less, or about 5, 10, 15, 20, 25, 30, 35, 40, 45, 50, 55, 60, 65, 70, 75, 80, 85, or about 90 wt % or more.

The emulsifier may include may include about 60 wt % to about 97 wt % polyaminated fatty acids, about 10 wt % to about 30 wt % hydrotreated light petroleum distillate, about 1 wt % to about 5 wt % ethylene glycol monobutyl ether, and about 1 wt % to about 5 wt % diethylene glycol monobutyl ether.

As previously mentioned, the treatment fluid may further comprise an aqueous acidic phase, which may comprise an acid, water, and a surface modification agent. The aqueous acid phase may be any suitable proportion of the emulsion. For example, the treatment fluid may about 10 wt % to about 99 wt % of the aqueous acid phase, or about 40 wt % to about 90 wt %, or about 10 wt % or less, or about 15 wt %, 20, 25, 30, 35, 40, 45, 50, 55, 60, 65, 70, 75, 80, 85, or about 90 wt % or more of the aqueous acid phase.

The water may be from any source provided that it does not contain an excess of compounds that may undesirably affect other components in the treatment fluid or the subterranean formation. The water may comprise freshwater or non-freshwater. Non-freshwater sources of water can include surface water ranging from brackish water to seawater, brine, returned water (sometimes referred to as flowback water) from the delivery of a well fluid into a well, unused well fluid, and produced water. The amount of the water may typically be dictated by the final concentration of acid desired. With the benefit of this disclosure one of ordinary skill in the art should recognize the appropriate type and amount of the water for a chosen application.

The acid may comprise organic acids, inorganic acids, derivatives thereof, or combinations thereof. Examples of suitable acids include, but are not limited to, hydrochloric acid, formic acid, lactic acid, phosphoric acid, sulfamic acid, acetic acid, derivatives thereof, and mixtures thereof. As will be appreciated by those of ordinary skill, with the benefit of this disclosure, acid-generating materials may also be used. The acid may be present in the aqueous acid phase in any suitable amount, including in an amount of from about 0.5 wt % to about 40 wt % of the aqueous acid phase. Alternatively, the acid may be present in the aqueous acid in an amount of from about 2.5 wt % to about 28 wt % of the aqueous acid phase, or from about 7.5 wt % to about 28 wt % of the aqueous acid phase, or from about 15 wt % to about 28 wt % of the aqueous acid or about 0.5, 1, 2, 3, 4, 5, 10, 15, 20, 25, 30, 35, or 40 wt %. Individuals skilled in the art, with the benefit of this disclosure, should be able to select a suitable acid and a suitable concentration thereof for a chosen application. In some instances, the particular concentration used in any particular embodiment depends on what acid is being used, and what percentage of acid is present. Other complex, interrelated factors that may be considered in deciding how much of the acid to use include, but are not limited to, the composition of the formation, the temperature of the formation, the particular fines and damage present in the formation (e.g., scale, skin, calcium carbonate, silicates, and the like), the particular acid used, metals the acid may contact, corrosion concerns, the expected contact time of the acid with the formation, etc.

A surface modification agent may be included in the aqueous acidic phase of the treatment fluid. Without being limited by theory, it is believed that, once introduced into the formation and the emulsion breaks, the surface modification agent interacts with rock surfaces in the treated portion of the carbonate formation. Any the surface modification agent may interact with the carbonate formation via a variety of different mechanisms, including without limitation adsorption and ion pairing, among others. By placement of the surface modification agent in the internal aqueous acidic phase of invert emulsions, it may be prevented from preferentially interacting at short distances in the treated formation, allowing for greater penetration of the surfactant. The interaction of the surface modification agent with the carbonate formation should modify the wettability of the formation to water wet. Additionally, the surface modification agents may also minimize capillary pressure in the formation, thus increasing the volume of spent acid and hydrocarbons recovered from the subterranean formation.

The potential impact of including the surface modification agents in the treatment fluid on the wettability of a formation can be examined by measuring the flow rate of the spent acid containing surface modification agents, followed by crude oil, through a vertical column. By way of example, the testing performed in Example 3 herein illustrates the impact on wettability due to inclusion of surface modifications agents in the treatment fluid. As illustrated, more of the spent acid passes through the vertical carbonate column treated with the surface modification agents than without treatment. This suggests that treatment with the surface modification agents could potentially leave a formation water wet, and minimize capillary pressure, increasing recovery of spent acid and hydrocarbons from carbonate formations.

The surface modification agents may be cationic surfactants, anionic surfactants, nonionic surfactants, or zwitterionic surfactants, as desired for a specification application. Examples of suitable cationic surfactants may include C12 to C18 mono-alkyl quaternary ammonium bromides and chlorides, such as cetyl trimethyl ammonium bromide, dodecyl trimethyl ammonium bromide, and cetyl pyridinium chloride. Examples of suitable anionic surfactants may include sulfates, sulfonates, and disulfonates. Additional examples may include alkyl ethoxylated sulfates, alkyl propoxylated sulfates, alkylbenzene sulfonates, alpha olefin sulfates, and internal olefin sulfonates. Examples of suitable nonionic surfactants may include a hydrocarbon chain attached to EO groups (ethoxy or CH2CH2-). The surface modification agent may comprise a blend of one or more surfactants. Individuals skilled in the art, with the benefit of this disclosure, should be able to select a suitable surface modification agent and a suitable concentration thereof for a chosen application. A number of factors may be considered in deciding the particular surface modification agent to use, including the composition of the formation, the type of emulsion, the particular emulsifier used, molecular weight, oil-phase solubility, etc.

The surface modification agent may comprise an alcohol surfactant blend, such as a blend of an alcohol (e.g., methanol, ethanol, etc.) and one or more surfactants. By way of example, the surface modification agent may comprise about 1 wt % to about 90 wt % alcohol, or about 50 wt % to about 90 wt % alcohol, or about 1, 5, 10, 15, 20, 25, 30, 35, 40, 45, 50, 55, 60, 65, 70, 75, 80, 85, or about 90 wt % or more of an alcohol. The alcohol surfactant blend may comprise about 5 wt % to about 10 wt % alkylbenzene sulfonate compound with 2-propanamine, 5 wt % to about 10 wt % alkylbenzene sulfonate compound with triethanolamine, and about 60% wt % to about 100 wt % methanol. Alternatively, the alcohol surfactant blend may comprise about 10 wt % to about 30 wt % C12-C16 ethoxylated alcohols and about 10 wt % to about 30 wt % methanol.

A surface modification agent should also be selected that does not undesirably interfere with emulsion stability. Generally, inclusion of additional surfactants is undesired in an emulsion acid formulation due to the tendency of many surfactants to destabilize emulsions, for example, by altering properties of the original emulsifier and destabilizing the emulsion. However, by selection of an appropriate surface modification agent, the benefits from its inclusion can be achieved without detrimentally impacting the emulsion. The potential impact of including the surface modification agents in the treatment fluid can be examined by emulsion stability testing. As illustrated in Examples 1 and 2 herein, surface modification agents can be selected that do not undesirably interfere with emulsion stability.

The surface modification agent may be present in the treatment fluid in an amount suitable for particular application. For example, the surface modification agent may be present in the treatment fluid in an amount of about 0.01 wt % or greater. By way of further example, the surface modification agent may be present in an amount of about 0.01 wt % to about 10 wt % or about 0.5 wt % to about 2 wt %, or about 0.01, 0.1, 0.5, 1, 2, 3, 4, 5, 6, 7, 8, 9, or 10 wt %.

Those of ordinary skill in the art, with the benefit of this disclosure, should appreciate that additional additives may be included in the treatment fluids as desired for a particular application. Examples of suitable additives may include corrosion inhibitors, freezing-point depressants, anti-oxidants, polymer degradation prevention additives, relative permeability modifiers, scale inhibitors, antifoaming agents, iron control agents, proppants or other particulates, particulate diverters, salts, fluid loss control additives, dispersants, flocculants, scavengers (e.g., $H_2S$ scavengers, $CO_2$ scavengers or $O_2$ scavengers), lubricants, breakers, friction reducers, bridging agents, weighting agents, solubilizers, pH control agents (e.g., buffers), hydrate inhibitors, bactericides, and the like. Combinations of these additives can be used as well.

As will be appreciated, the treatment fluids may be used in a variety of applications where acidizing with a treatment fluid comprising a surface modification agent may be desired. The purpose of acidizing is to dissolve acid-soluble materials. A treatment fluid in the form of an emulsion comprising a hydrocarbon phase, an aqueous acidic phase, an emulsifier and a water wetting surfactant may be provided. The treatment fluid may be introduced into a subterranean formation by way of a wellbore to dissolve the acid-soluble materials. In this way, oil or gas can more easily flow from the formation into the wellbore. In addition, acidizing can facilitate the flow of injected treatment fluids from the well into the formation.

Acidizing operations may be carried out as acid fracturing procedures or matrix acidizing procedures. In acid fracturing, a treatment fluid in the form of an emulsion comprising a hydrocarbon phase, an aqueous acidic phase, an emulsifier and a water wetting surfactant a treatment fluid may be provided and pumped into a formation at a sufficient pressure to cause fracturing of the formation and to create differential (non-uniform) etching of fracture conductivity. For example, the treatment fluid may be introduced into the formation to cause fracturing of the formation. Depending on the rock of the formation, the treatment fluid can etch the fractures faces, whereby flow channels may be formed when the fractures close. The treatment fluid may also enlarge the pore spaces in the fracture faces and in the formation. In matrix acidizing, the treatment fluid may be injected from the wellbore into the formation at a rate and pressure below the pressure sufficient to create a fracture in the formation.

A method of acidizing a subterranean formation may be provided. The method may comprise providing a treatment fluid in the form of an invert emulsion, wherein the treatment fluid comprises: a hydrocarbon phase; and an aqueous acidic phase comprising water, an acid, and a surface modification agent. The method may further comprise introducing the treatment fluid into a wellbore. The method may further comprise acidizing the subterranean formation to dissolve acid-soluble materials in the subterranean formation. The treatment fluid may be introduced into the subterranean formation surrounding the wellbore such that one or more fractures are formed in the subterranean formation. The hydrocarbon phase may be about 10% to about 50% of the treatment fluid by volume. The hydrocarbon phase may comprise at least one liquid selected from the group consisting of kerosene, diesel oil, crude oil, gas oil, fuel oil, paraffin oil, mineral oil, olefinic hydrocarbon, aromatic hydrocarbon, glyceride triester, other petroleum distillates, and any combination thereof. The hydrocarbon phase may comprise an aromatic hydrocarbon composition. The acid may be selected from the group consisting of hydrochloric acid, formic acid, lactic acid, phosphoric acid, sulfamic acid, acetic acid, derivatives thereof, and mixtures thereof, and wherein the acid is present in an amount of from about 0.5% to about 40% by weight of the aqueous acid phase. The surface modification agent may present in the treatment fluid in an amount of about 0.01% to about 10% by weight of the treatment fluid. The hydrocarbon phase may comprise an emulsifier. The emulsifier may comprise ethylene glycol monobutyl ether, diethylene glycol monobutyl ether, and hydrotreated light petroleum distillate. The surface modification agent may comprise at least one surfactant selected from the group consisting of a C12 to C18 mono-alkyl quaternary ammonium bromide, a C12 to C18 mono-alkyl quaternary ammonium chloride, cetyl trimethyl ammonium bromide, dodecyl trimethyl ammonium bromide, cetyl pyridinium chloride, a sulfate, a sulfonate, a disulfonate, an alkyl ethoxylated sulfate, an alkyl propoxylated sulfate, an alkylbenzene sulfonate, an alpha olefin sulfate, an internal olefin sulfonate. The surface modification agent may comprise an alcohol surfactant blend, wherein the alcohol surfactant blend comprises an alkylbenzene sulfonate compound with 2-propanamine in an amount of about 5% to about 10% by weight of the alcohol surfactant blend, an alkylbenzene sulfonate compound with triethanolamine in an amount of about 5% to about 10% by weight of the alcohol surfactant blend, and methanol in an amount of about 60% to about 100% by weight of the alcohol surfactant blend. The surface modification agent may comprise an alcohol surfactant blend, wherein the alcohol surfactant blend comprises a C12-C16 ethoxylated alcohol in an amount of about 10% to about 30% by weight of the alcohol surfactant blend and methanol in an amount of about 10% to about 30% by weight of the alcohol surfactant blend.

A treatment fluid may be provided comprising: a hydrocarbon phase comprising an oil-soluble liquid and an emulsifier; and an aqueous acidic phase comprising water, an acid, and a surface modification agent, wherein the treatment fluid is in the form of an invert emulsion. The hydrocarbon phase may be about 10% to about 50% of the treatment fluid by volume. The hydrocarbon phase may comprise at least one liquid selected from the group consisting of kerosene, diesel oil, crude oil, gas oil, fuel oil, paraffin oil, mineral oil, olefinic hydrocarbon, aromatic hydrocarbon, glyceride triester, other petroleum distillates, and any combination thereof. The hydrocarbon phase may comprise an aromatic hydrocarbon composition. The acid may be selected from the group consisting of hydrochloric acid, formic acid, lactic acid, phosphoric acid, sulfamic acid, acetic acid, derivatives thereof, and mixtures thereof, and wherein the acid is present in an amount of from about 0.5% to about 40% by weight of the aqueous acid phase. The surface modification agent may present in the treatment fluid in an amount of about 0.01% to about 10% by weight of the treatment fluid. The hydrocarbon phase may comprise an emulsifier. The emulsifier may comprise ethylene glycol monobutyl ether, diethylene glycol monobutyl ether, and hydrotreated light petroleum distillate. The surface modification agent may comprise at least one surfactant selected from the group consisting of a C12 to C18 mono-alkyl quaternary ammonium bromide, a C12 to C18 mono-alkyl quaternary ammonium chloride, cetyl trimethyl ammonium bromide, dodecyl trimethyl ammonium bromide, cetyl pyridinium chloride, a sulfate, a sulfonate, a disulfonate, an alkyl ethoxylated sulfate, an alkyl propoxylated sulfate, an alkylbenzene sulfonate, an alpha olefin sulfate, an internal olefin sulfonate. The surface modification agent may comprise an alcohol surfactant blend, wherein the alcohol surfactant blend comprises an alkylbenzene sulfonate compound with 2-propanamine in an amount of about 5% to about 10% by weight of the alcohol surfactant blend, an alkylbenzene sulfonate compound with triethanolamine in an amount of about 5% to about 10% by weight of the alcohol surfactant blend, and methanol in an amount of about 60% to about 100% by weight of the alcohol surfactant blend. The surface modification agent may comprise an alcohol surfactant blend, wherein the alcohol surfactant blend comprises a C12-C16 ethoxylated alcohol in an amount of about 10% to about 30% by weight of the alcohol surfactant blend and methanol in an amount of about 10% to about 30% by weight of the alcohol surfactant blend.

A system for introducing a treatment fluid into a wellbore may be provided that comprises a fluid handling system containing the treatment fluid, wherein the treatment fluid is in the form of an emulsion and comprises a hydrocarbon phase and an aqueous acidic phase, wherein the aqueous acidic phase comprises water, an acid, and a surface modification agent; and a tubular in a wellbore in a subterranean formation, wherein the tubular is in fluid communication with the fluid handling system. The fluid handling system may comprise pumping equipment and a fluid supply. The hydrocarbon phase may be about 10% to about 50% of the treatment fluid by volume. The hydrocarbon phase may comprise at least one liquid selected from the group consisting of kerosene, diesel oil, crude oil, gas oil, fuel oil, paraffin oil, mineral oil, olefinic hydrocarbon, aromatic hydrocarbon, glyceride triester, other petroleum distillates, and any combination thereof. The hydrocarbon phase may comprise an aromatic hydrocarbon composition. The acid may be selected from the group consisting of hydrochloric acid, formic acid, lactic acid, phosphoric acid, sulfamic acid, acetic acid, derivatives thereof, and mixtures thereof, and wherein the acid is present in an amount of from about 0.5% to about 40% by weight of the aqueous acid phase. The surface modification agent may present in the treatment fluid in an amount of about 0.01% to about 10% by weight of the treatment fluid. The hydrocarbon phase may comprise an emulsifier. The emulsifier may comprise ethylene glycol monobutyl ether, diethylene glycol monobutyl ether, and hydrotreated light petroleum distillate. The surface modification agent may comprise at least one surfactant selected from the group consisting of a C12 to C18 mono-alkyl quaternary ammonium bromide, a C12 to C18 mono-alkyl quaternary ammonium chloride, cetyl trimethyl ammonium bromide, dodecyl trimethyl ammonium bromide, cetyl pyridinium chloride, a sulfate, a sulfonate, a disulfonate, an alkyl ethoxylated sulfate, an alkyl propoxylated sulfate, an alkylbenzene sulfonate, an alpha olefin sulfate, an internal olefin sulfonate. The surface modification agent may comprise an alcohol surfactant blend, wherein the alcohol surfactant blend comprises an alkylbenzene sulfonate compound with 2-propanamine in an amount of about 5% to about 10% by weight of the alcohol surfactant blend, an alkylbenzene sulfonate compound with triethanolamine in an amount of about 5% to about 10% by weight of the alcohol surfactant blend, and methanol in an amount of about 60% to about 100% by weight of the alcohol surfactant blend. The surface modification agent may comprise an alcohol surfactant blend, wherein the alcohol surfactant blend comprises a C12-C16 ethoxylated alcohol in an amount of about 10% to about 30% by weight of the alcohol surfactant blend and methanol in an amount of about 10% to about 30% by weight of the alcohol surfactant blend.

Turning now to the FIGURE, an example well system 100 for introduction of treatment fluids described herein into a wellbore 105 is shown. As depicted in the FIGURE, system 100 may include a fluid handling system 110 for introducing an emulsified acidic treatment fluid 115 into the wellbore by way of tubular 120. In the illustrated embodiment, the fluid handling system 110 is above the surface 125 while wellbore 105 and tubular 120 are below the surface 125. The fluid handling system 110 can be configured as shown in the FIGURE or in a different manner, and may include additional or different features as appropriate. The fluid handling system 110 may be deployed via skid equipment, marine vessel deployed or may be comprised of sub-sea deployed equipment.

As illustrated in the FIGURE, wellbore 105 may include vertical and horizontal sections and an emulsified acidic treatment fluid 115 may be introduced into subterranean formation 130 surrounding the horizontal portion of the wellbore 105. Generally, a wellbore may include horizontal, vertical, slant, curved, and other types of wellbore geometries and orientations, and the treatment fluid 115 may generally be applied to subterranean formation 130 surrounding any portion of wellbore 105. Wellbore 105 may include a casing that is cemented or otherwise secured to the wellbore wall. Wellbore 105 can be uncased or include uncased sections. Perforations can be formed in the casing to allow treatment fluids and/or other materials to flow into subterranean formation 130. Perforations can be formed using shape charges, a perforating gun, and/or other tools.

Fluid handling system 110 may include mobile vehicles, immobile installations, skids, hoses, tubes, fluid tanks or reservoirs, pumps, valves, and/or other suitable structures and equipment. For example, the fluid handling system 110 may include pumping equipment 135 and a fluid supply 140, which both may be in fluid communication with the tubular 120. The fluid supply 140 may contain the emulsified aqueous acidic treatment fluid 115. The pumping equipment 135 may be used to supply treatment fluid 115 from the fluid supply 140, which may include tank, reservoir, connections to external fluid supplies, and/or other suitable structures and equipment. Pumping equipment 135 may be coupled to tubular 120 to communicate treatment fluid 115 into wellbore 105. Fluid handling system 110 may also include surface and down-hole sensors (not shown) to measure pressure, rate, temperature and/or other parameters of treatment. Fluid handling system 110 may include pump controls and/or other types of controls for starting, stopping and/or otherwise controlling pumping as well as controls for selecting and/or otherwise controlling fluids pumped during the injection treatment. An injection control system may communicate with such equipment to monitor and control the injection treatment.

The tubular 120 may include coiled tubing, sectioned pipe, and/or other structures that communicate fluid through wellbore 105. Alternatively, tubular may include casing, liners, or other tubular structures disposed in wellbore 105. Tubular 120 may include flow control devices, bypass valves, ports, and or other tools or well devices that control a flow of fluid from the interior of tubular 120 into subterranean formation 130. For example, tubular 120 may include ports to communicate treatment fluid 130 directly into the rock matrix of the subterranean formation 130. Although FIG. 1 shows the horizontal section of the tubular 120 represents an inner tubular structure of well system 100, in some embodiments, such inner tubular structure may be absent.

With continued reference to FIG. 1, well system 100 may be used for delivery of the emulsified acidic treatment fluid 115 into wellbore 105. The emulsified acidic treatment fluid 115 may be pumped from fluid supply 140 down the interior of tubular 120 in wellbore 105. Emulsified acidic treatment fluid 115 may be allowed to flow down the interior of tubular 120, exit the tubular 120, and finally enter subterranean formation 130 surrounding wellbore 105. Emulsified acidic treatment fluid 130 may dissolve acid soluble portions of subterranean formation 130. Emulsified acidic treatment fluid 130 may also enter subterranean formation 130 at a sufficient pressure to cause fracturing of subterranean formation 130. The surface modification agent(s) contained in the emulsified acidic treatment fluid 130 may adhere to rock surfaces within the subterranean formation 130, for example, after breaking of the emulsion. By placement in the subterranean formation 130, the surface modification agent(s) may leave water-wet surfaces in the subterranean formation 130 which would otherwise be naturally oil wet.

It is also to be recognized that the disclosed treatment fluids may also directly or indirectly affect the various downhole equipment and tools that may come into contact with the treatment fluids during operation. Such equipment and tools may include, but are not limited to, wellbore casing, wellbore liner, completion string, insert strings, drill string, coiled tubing, slickline, wireline, drill pipe, drill collars, mud motors, downhole motors and/or pumps, surface-mounted motors and/or pumps, centralizers, turbolizers, scratchers, floats (e.g., shoes, collars, valves, etc.), logging tools and related telemetry equipment, actuators (e.g., electromechanical devices, hydromechanical devices, etc.), sliding sleeves, production sleeves, plugs, screens, filters, flow control devices (e.g., inflow control devices, autonomous inflow control devices, outflow control devices, etc.), couplings (e.g., electro-hydraulic wet connect, dry connect, inductive coupler, etc.), control lines (e.g., electrical, fiber optic, hydraulic, etc.), surveillance lines, drill bits and reamers, sensors or distributed sensors, downhole heat exchangers, valves and corresponding actuation devices, tool seals, packers, cement plugs, bridge plugs, and other wellbore isolation devices, or components, and the like. Any of these components may be included in the systems generally described above and depicted in FIG. 1.

EXAMPLES

To facilitate a better understanding of the present invention, the following examples of certain aspects of some embodiments are given. In no way should the following examples be read to limit, or define, the entire scope of the invention.

Example 1

The following example was performed to demonstrate the stability of oil-in water emulsions prepared with different surface modification agents. Test No. 1 used an alcohol surfactant blend referred to as "SMA 1," which comprised about 10 wt % to about 30 wt % C12-C16 ethoxylated alcohols and about 10 wt % to about 30 wt % methanol. Test No. 2 used an alcohol surfactant blend referred to as "SMA 2," which comprised about 5 wt % to about 10 wt % alkylbenzene sulfonate compound with 2-propanamine, 5 wt % to about 10 wt % alkylbenzene sulfonate compound with triethanolamine, and about 60 wt % to about 100 wt % methanol.

The hydrocarbon phase of the emulsions was prepared by mixing an emulsifier with diesel in a Waring blender jar. An aqueous acid solution comprising 7.5% hydrochloric acid by weight was added to the hydrocarbon phase very slowly with stirring. Once the addition was completed, the blend was mixed for 10 to 15 minutes in a high speed Waring blender (9000 rpm) to form a water-in-oil emulsion. The water-in-oil emulsion had a hydrocarbon phase to water phase ratio of 28:72 OWR v/v. The emulsifier used in this example was a mixture of ethylene glycol monobutyl ether, diethylene glycol monobutyl ether, and hydrotreated light petroleum distillate, which was present in an amount of 2% by volume of the emulsion.

The emulsions used in tests had the following composition. In the following table, the abbreviation gals/1000 gals refers to gallons per thousand gallons of the water phase.

TABLE 1

Emulsion Composition.

| Additive | Test 1 | Test 2 |
|---|---|---|
| Fresh water | 528.9 gals/1000 gals | 528.9 gals/1000 gals |
| SMA 1 | 2 gals/1000 gals | |
| SMA 2 | | 2 gals/1000 gals |
| Emulsifier | 20 gals/1000 gals | 20 gals/1000 gals |
| KCl | 607 lbs/1000 gals | 607 lbs/1000 gals |
| Diesel | 260 gals/1000 gals | 260 gals/1000 gals |
| Acid (7.5% HCl) | 153 gals/1000 gals | 153 gals/1000 gals |

To test emulsion stability, the different surface modification agents at 2 gallons per thousand gallons (gal/1000 gals) were separately added to the internal water phase of the emulsion before mixing the emulsion. The emulsion stability of these emulsions was evaluated by visual observation of the emulsions kept in sealed jars at room temperature and also in a high temperature water bath. Any separation of the hydrocarbon phase and aqueous acidic phase was considered as destabilization. After 5 days at room temperature, the emulsions were stable with no visible separation. The emulsions were then immersed in a water bath for 3 hours at 180° F. after which no separation was observed. The final viscosities after this stability test were 180 cp and 160 cp (@ 300 rpm Fann 35 viscometer) for Test No. 1 with the SMA 1 and Test No. 2 with the SMA 2, respectively.

Example 2

Additional emulsion stability tests were performed to further evaluate the stability of invert emulsions in the presence of surface modification agents. Test No. 3 used SMA 1. Test No. 4 used a non-ionic surfactant referred to as "SMA 3," which comprised a blend of about 10 wt % to about 30 wt % of a light aromatic solvent, about 5 wt % to about 10 wt % of ethoxylated nonylphenol, and about 30 wt % to about 60 wt % of isopropanol. Test No. 5 used a cationic surfactant referred to as "SMA 4," which comprised a blend of about 30 wt % to about 60 wt % of quaternary ammonium compounds, about 5 wt % to about 10 wt % of isopropanol, and about 30 wt % to about 60 wt % of methanol.

To test emulsion stability, 2 ml of each surface modification agents listed above were separately added to 50 ml of an invert emulsion acid containing no surface modification agents initially:

TABLE 2

| Additive | Concentration (gals/1000 gals) |
|---|---|
| Fresh Water | 530.4 |
| Emulsifier | 20 |
| KCl (7% by wt) | 607 |
| Diesel | 260 |
| Raw Acid (7.5% by wt) | 153 |

The emulsion stability was evaluated by visual observation of the emulsions kept in sealed jars after addition of the surface modification agent. Any separation of the oil and aqueous acidic phases was considered as destabilization. After 30 minutes at room temperature, the emulsions for Test No. 4 with the SMA 3 and Test No. 5 with the SMA 4 surfactant completely separated. The emulsion for Test No. 3 with the SMA 1 was stable for several days.

Example 3

Column flow testing was performed to evaluate the surface wettability modification and reduction in capillary pressure of certain surface modification agents. The column flow testing used three carbonate columns that each comprised 10 grams of 100% carbonate rock in separate 15 milliliter glass tubes. The carbonate rock had a particle size of −40+50 mesh, US Sieve Series. The carbonate columns were each conditioned with spent acid with the pH adjusted to 4 and then tested to determine column flow.

The conditioning procedures for each column is as follows: 1) Add the spent acid to the glass tube up to the 15-millileter mark; 2) Run three pore volumes of the same spent acid through the carbonate column in the glass tube; 3) close the tubing clamp at the bottom of the glass tube after the three pore volumes have been run; and 4) pipette out the remaining spent acid from the glass tube such that the meniscus of the spent acid should stop just above the top of the carbonate column.

After the carbonate columns were conditioned, the testing was performed by first adding crude oil to the glass tubing up to the 15 milliliter mark. Fluid exit from the bottom of the glass tubes were controlled with tubing clamps at the bottom of the glass tubes. The tubing clamps were opened while simultaneously measuring the time until the oil breaks through the first column. The spent acid was allowed to drain from the bottom of the glass tubes for a period of approximately 1 minute when the testing was interrupted simultaneously for all three columns when the crude oil level in column 2 broke through the carbonate column. For each column, the amount of fluid that drained from the corresponding glass tube was observed. During this testing, no external pressure was applied to the carbonate columns. The column flow testing was performed for three different carbonate columns. The spent acid added to column 1 did not include a surface modification agent. The spent acid added to column 2 included SMA 1 at a concentration of 2 gal/1000 gals. The spent acid added to column 3 included SMA 2 at a concentration of 2 gal/1000 gals. The results of this test are provided in the table below. In the following table, the abbreviation gal/1000 gals refers to gallons per thousand gallons of the water phase.

TABLE 3

| Test Column | Surface modification agent | | Spent Acid Flow (ml) |
|---|---|---|---|
| | Type | Concentration | |
| 1 | — | — | 4 |
| 2 | SMA 1 | 2 gal/1000 gals | 6 |
| 3 | SMA 2 | 2 gal/1000 gals | 8 |

As illustrated, inclusion of the surface modification agents in the spent acid increased the flow rate of spent acid and crude oil that could flow through the carbonate column, indicating that changing the wettability and reducing capillary pressure in the pores can increase the volume of spent acid and volume of crude oil recovered from a formation.

Therefore, the present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention. While compositions and methods are described in terms of "comprising," "containing," "having," or "including" various components or steps, the compositions and methods can also "consist essentially of" or "consist of" the various components and steps. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee.

What is claimed is:

1. A method of acidizing a subterranean formation, comprising:
   providing a treatment fluid in the form of an invert emulsion, wherein the treatment fluid comprises:
   a hydrocarbon phase; and
   an aqueous acidic phase comprising water, an acid, wherein the acid is present in an amount of about 0.5% to about 10% by weight of the aqueous acidic phase, and a surface modification agent comprising an internal olefin sulfonate, wherein the internal olefin sulfonate is present in an amount of about 5% to about 10% by weight of the treatment fluid; wherein the aqueous acidic phase is present in the treatment fluid in an amount of about 60% to about 99% based on a total weight of the treatment fluid; wherein the hydrocarbon phase to water phase ratio is about 20:80 to about 30:70 oil to water ratio by volume;
   introducing the treatment fluid into a wellbore;
   breaking the invert emulsion and thereafter exposing the subterranean formation to the surface modification agent; and
   changing wettability of carbonate portions of the subterranean formation from oil-wet to water-wet with the surface modification agent.

2. A method according to claim 1 further comprising acidizing the subterranean formation to dissolve acid-soluble materials in the subterranean formation.

3. A method according to claim 1, wherein the treatment fluid is introduced into the subterranean formation surrounding the wellbore such that one or more fractures are formed in the subterranean formation.

4. A method according to claim 1, wherein the hydrocarbon phase is about 10% to about 50% of the treatment fluid by volume.

5. A method according to claim 1, wherein the hydrocarbon phase comprises at least one liquid selected from the group consisting of kerosene, diesel oil, crude oil, gas oil, fuel oil, paraffin oil, mineral oil, olefinic hydrocarbon, aromatic hydrocarbon, glyceride triester, petroleum distillates, and any combination thereof.

6. A method according to claim 1, wherein the acid is selected from the group consisting of hydrochloric acid, formic acid, lactic acid, phosphoric acid, sulfamic acid, acetic acid, derivatives thereof, and mixtures thereof.

7. A method according to claim 1, wherein the surface modification agent further comprises at least one surfactant selected from the group consisting of a C12 to C18 monoalkyl quaternary ammonium bromide, a C12 to C18 monoalkyl quaternary ammonium chloride, cetyl trimethyl ammonium bromide, dodecyl trimethyl ammonium bromide, cetyl pyridinium chloride, a sulfate, a sulfonate, a disulfonate, an alkyl ethoxylated sulfate, an alkyl propoxylated sulfate, an alkylbenzene sulfonate, an alpha olefin sulfate, and combinations thereof.

8. The method of claim 1, further comprising increasing spent acid flowback.

9. A method according to claim 1, wherein the hydrocarbon phase comprises an emulsifier mixed with paraffin oil.

10. A method according to claim 1, wherein the hydrocarbon phase has a viscosity of less than 200 cP.

11. A method according to claim 1, wherein the hydrocarbon phase has a viscosity of less than 20 cP.

* * * * *